(12) United States Patent
Duvall et al.

(10) Patent No.: US 10,414,891 B2
(45) Date of Patent: Sep. 17, 2019

(54) POLYURETHANE CURATIVES

(71) Applicant: The Shepherd Chemical Company, Cincinnati, OH (US)

(72) Inventors: Tod C. Duvall, West Chester, OH (US); Jeffrey Sullivan, Goshen, OH (US); Nathan Eckert, Loveland, OH (US)

(73) Assignee: The Shepherd Chemical Company, Cincinnati, OH (US)

( * ) Notice: Subject to any disclaimer, the term of this patent is extended or adjusted under 35 U.S.C. 154(b) by 0 days.

(21) Appl. No.: 14/964,773

(22) Filed: Dec. 10, 2015

(65) Prior Publication Data

US 2016/0200888 A1    Jul. 14, 2016

Related U.S. Application Data

(60) Provisional application No. 62/102,726, filed on Jan. 13, 2015.

(51) Int. Cl.

| | |
|---|---|
| *C07F 5/00* | (2006.01) |
| *C08G 18/16* | (2006.01) |
| *C08G 18/20* | (2006.01) |
| *C08G 18/22* | (2006.01) |
| *C08G 18/40* | (2006.01) |
| *C08G 18/42* | (2006.01) |
| *C08G 18/48* | (2006.01) |
| *C08G 18/54* | (2006.01) |
| *C08G 18/76* | (2006.01) |
| *C08J 9/00* | (2006.01) |
| C08G 101/00 | (2006.01) |

(52) U.S. Cl.
CPC .............. *C08J 9/00* (2013.01); *C07F 5/003* (2013.01); *C08G 18/161* (2013.01); *C08G 18/2081* (2013.01); *C08G 18/227* (2013.01); *C08G 18/4027* (2013.01); *C08G 18/42* (2013.01); *C08G 18/48* (2013.01); *C08G 18/546* (2013.01); *C08G 18/7621* (2013.01); C08G 2101/0008 (2013.01); C08G 2101/0016 (2013.01); C08G 2101/0025 (2013.01); C08G 2101/0083 (2013.01); C08G 2290/00 (2013.01); *C08J 2475/04* (2013.01); *C08J 2475/06* (2013.01); *C08J 2475/08* (2013.01)

(58) Field of Classification Search
CPC ................ C08G 18/227; C08G 18/161; C08G 18/2081; C08G 18/4027; C08G 18/42; C08G 18/48; C08G 18/546; C08G 18/7621; C08G 2101/0008; C08G 2101/0016; C08G 2101/0025; C08G 2101/0083; C08G 2290/00; C07F 5/003; C08J 9/00; C08J 2475/04; C08J 2475/06; C08J 2475/08

See application file for complete search history.

(56) References Cited

U.S. PATENT DOCUMENTS

| | | | | |
|---|---|---|---|---|
| 4,788,083 | A * | 11/1988 | Dammann ........... | C08G 18/089 427/340 |
| 5,587,448 | A * | 12/1996 | Engen .................... | C08G 18/08 427/290 |
| 2004/0147626 | A1* | 7/2004 | Hohl ..................... | C08G 18/227 521/155 |
| 2010/0249359 | A1* | 9/2010 | Tulloch ................. | C07C 215/14 528/51 |

FOREIGN PATENT DOCUMENTS

| | | |
|---|---|---|
| CA | 2049695 A1 | 2/1993 |
| EP | 2604615 A1 | 6/2013 |

OTHER PUBLICATIONS

International Search Report and Written Opinion for PCT Application No. PCT/US2015/064950, dated Mar. 2, 2016.

* cited by examiner

*Primary Examiner* — Melissa A Rioja
(74) *Attorney, Agent, or Firm* — Frost Brown Todd LLC

(57) ABSTRACT

A class of alkanol amine ligands reacted with bismuth carboxylates lends unique curability properties to isocyanate and polyols for production of polyurethane for CASE applications, including growing demand for polyurethane sprayfoam. The amino-alcohol ligand, when associated with bismuth neodecanoate, offers improved moisture and solvent resistance during B-side (polyol) storage, cure rates analogous to tin-based curatives, and overall good final physical properties of the cured polyurethane.

2 Claims, 4 Drawing Sheets

POLYURETHANE CURATIVES

BACKGROUND

Urethane polymers or polyurethanes (PU's) are a large family of polymers with widely varying properties and uses, all based on the reaction product of an organic isocyanate with compounds containing a hydroxyl group. Polyurethane polymers are generally classified into two broad categories: foam or polyurethane foam, and elastomers or polyurethane elastomers. Polyurethane foams are urethane polymers produced by the reaction of polyisocyanates with a hydroxyl group from a polyol and a polymerization catalyst, in the presence of an auxiliary blowing agent, such as monofluorotrichloromethane or water, which allows the polymeric mass to expand into a cellular mass upon reaction. Polyurethane elastomers are produced by the reaction of an isocyanate with a hydroxyl group to form urethane linkages in the presence of a polymerization catalyst. No blowing agent or mechanism for producing gas which would lead to cell development is present.

Polyurethane elastomers have been widely used in a variety of applications. They have been used as protective coatings, as insulation of electrical elements, as caulks, sealants, gaskets, etc. Because of favorable rheology of an elastomer formulation, they can be used to cast intricate forms such as those found in the toy industry. They have also been widely used in the preparation of sporting goods, fabric coatings and shoe soles wherein the cured urethane elastomer comes in repeated intimate contact with human beings. The prior art catalysts used to prepare elastomers frequently contained toxic mercury and lead compounds and the toxicity was carried over into the cured elastomer. If less toxic organotin compounds are employed as catalysts, elastomers having physical properties less than optimum are obtained.

The production of rigid polyurethane foams is a well-known art, and as such, foams have a wide variety of industrial and commercial applications. Rigid PU foams have been used as packaging materials, flotation materials and various structural components. Rigid PU foam has one of the lowest thermal conductivity ratings of any insulant, which allows efficient retention of heat or, alternatively, maintenance of a refrigerated or frozen environment. Insulating rigid polyurethane foams may be molded into many useful appliances. The foams may be shaped into sheets of varying thickness and placed between roofs or in floors. They also may be formed into contour shapes useful in insulating pipes and ducts. Rigid polyurethane foam can also be applied to numerous substrates by spray foaming techniques. Spray foam applications are important particularly in such areas as warehouses, schools and offices providing the desired insulation requirements for heating and cooling. Polyurethanes are widely used in high resiliency flexible foam seating, rigid foam insulation panels, microcellular foam seals and gaskets, durable elastomeric wheels and tires, automotive suspension bushings, electrical potting compounds, high performance adhesives and sealants, Spandex fibers, seals, gaskets, carpet underlay, and hard plastic parts (such as for electronic instruments).

As a subclass of commercially available polymers, polyurethane elastomers have several properties whose advantages confer unique benefits on these products. Typically, polyurethanes show high abrasion resistance with high load bearing, excellent cut and tear resistance, high hardness, resistance to ozone degradation, yet are pourable and castable. Compared to metals, polyurethanes are lighter in weight, less noisy in use, show better wear and excellent corrosion resistance while being capable of cheap fabrication. Compared to other plastics, polyurethanes are non-brittle, much more resistant to abrasion, and exhibit good elastomeric memory. Polyurethanes can be used for coatings and adhesives, utilizing secondary amine curing agents. Among well-known catalysts used for controlling competing reactions are tertiary amines, organometallic compounds, alkali metal salts of carboxylic acids and carboxylic acids. Also, it may be considered known to cure polyurethane prepolymers with a curing system comprising a dialkyl aromatic secondary amine, a polyol and a primary amine at room temperature using a catalyst system comprising adipic acid and a tin catalyst. However, some applications, such as coatings or repairs, i.e., patches, for concrete structures, such as roads, bridge abutments, parking lots, etc., must also have a very low moisture sensitivity. Therefore, organotin catalysts, such as dibutyl tin dilaurate, or tin(2-ethylhexanoate)oxide, which catalyze the reaction of the prepolymer with water, can only be used in small amounts and care must be taken to keep exposure to moisture at a minimum.

Part of the utility of polyurethanes is derived from their enormous diversity of properties resulting from a relatively limited number of reactants. Typically, polyurethanes are prepared on site by curing urethane prepolymers, which are adducts of polyisocyanates and polyhydric compounds. A large class of such prepolymers are approximately 2:1 adducts of a diisocyanate, OCN—Y—NCO, and a diol, HO—Z—OH, whose resulting structure is OCN—Y—NHCO$_2$—Z—OCONH—Y—NCO. Y can vary greatly, but is usually a divalent alkyl, cyclohexyl, or aromatic radical. In fact the most available urethane prepolymers are made from 2,4-toluenediisocyanate (TDI), or 80/20 mixtures with 2,6-toluenediisocyanate or 4,4'-methylene-diphenyldiisocyanate (MDI). The diols forming the "backbone" of the polymer, containing the "soft segments," display a greater range of variety. For instance, Z may be a divalent alkyl radical (i.e., an alkylene group) and frequently is an ether or ester which are condensation products of glycols with alkylene oxides and dicarboxylic acids, respectively.

Polyureas are prepared in a similar manner as the polyurethane prepolymers described above except that the backbone of the polymer is formed by the reaction of a polyamine (rather than a polyol) with a diisocyanate. The polyamines and polyols used in the reaction will be referred to as "backbone" polyols or "backbone" polyamines to distinguish them from the curing agents of the present technology.

In the so-called "one-shot" process, a separate step of forming a prepolymer is eliminated and all reactants are brought together at the same time or substantially simultaneously. This term may also be applied where the typical "prepolymer" components are brought together first and within a very short time the curing agent and other additives are mixed together. The "one-shot" method of processing is particularly prevalent in MDI- or modified MDI-based systems. The process generally requires that the various components have similar reactivities with the isocyanate components. The higher heat of reaction creates limitations and some complications with larger cast parts or thicker coatings, but is not particularly deleterious or can be tolerated in the applications contemplated here, and, in fact, may be advantageous in promoting a faster cure without requiring the addition of heat.

Polyurethanes and polyureas are formed by curing the urethane prepolymer. Curing is the reaction of the terminal isocyanate groups of the prepolymer with active hydrogens of a polyfunctional compound so as to form high polymers through chain extension and, in some cases, cross-linking. Diols, especially alkylene diols, are the most common curing agents, especially for MDI-based urethane prepolymers, and representing such diols with the structure HO—X—OH, where X is an organic moiety, most usually an alkylene group, the resulting polymer has as its repeating unit, —Y—NHCO$_2$—Z—OCONH—Y—NHCO$_2$—X—OCONH—, where a triol or a higher polyhydric alcohol is used, cross-linking occurs to afford a nonlinear polymer.

Other polyfunctional chemicals, especially diamines, are suitable as a curing agent. For example, 4,4'-methylene-bis-ortho-chloroaniline, usually referred to as MOCA or MBOCA, is a primary diamine curing agent which is both a chain extender and a cross-linker for TDI-based urethane prepolymers. Generally, however, primary diamines react with prepolymers, and especially MDI-based prepolymers, so quickly that they are not usable as curing agents. Recently, certain secondary diamines have been found to have an acceptably long pot life, and act as chain extenders with urethane prepolymers. Such secondary diamines as N,N'-dialkyl-4,4'-methylene-dianilines, N,N'-dialkyl-phenylene-diamines, and polyfunctional oligomers based thereon, are generally effective curing agents for a broad range of urethane prepolymers at elevated temperatures. Polyhydric alcohols have also been used as curing agents because their reaction with urethane prepolymers is sufficiently fast to be convenient, but not so fast as to make it difficult to work with the resulting polymer. Previous attempts to cure polyurethane and polyurea coatings at ambient temperature have involved the use of a curing agent which includes a primary amine which, as mentioned above, cure very quickly.

Polyurethanes find extensive application as coatings and adhesives. Polyurethanes are particularly desirable because of their chemical resistance, light stability, flexibility, toughness, weatherability, moisture resistance, abrasion resistance, gloss and color retention, and impact resistance. For polymers used in coating or adhesive applications, it is desirable that the tack-free time be reasonably short, i.e., within about 48 hours or preferably within about 18 hours, and gel time long enough for the material to be coated onto a substrate.

Virtually all commercially manufactured polyurethane foams are prepared using at least one catalyst. Catalysts are those compounds that help promote the reaction between an isocyanate and an isocyanate-reactive compound. The types of catalysts that are typically utilized in the formation of rigid polyurethane foams may differ depending on application.

Although organometallic catalysts have found acceptance in many commercial coatings, adhesives, sealants, and elastomers (CASE) applications, their use in urethane-based flexible and semi-flexible foams is limited. Tertiary amines are currently the industry standard polyurethane foam catalyst, but their distinct odor and volatility has caused scientists to search for alternate catalysts.

BRIEF SUMMARY

The reaction of isocyanates and polyols leads to the formation of polyurethanes. To initiate and accelerate the conversion of the above mentioned starting materials, a catalyst is often used. Many catalysts contain metals such as Sn, Hg, Bi. Alternatively, other catalysts do not contain metals and these may include tertiary amines. Of the metals available for use as a polyurethane catalyst, a metal selected from either bismuth or zinc, may have the lowest toxicity. Yet, the use of these catalysts, such as Bi NDA (neodecanoate) (bismuth carboxylate), often presents problems in that the bismuth-based catalysts either cure too quickly and/or have poor backend cure.

It has been discovered, that when using alkanolamine ligands in conjunction with Bi NDA, greater curative control of the bismuth species is obtained through complexation-type species with associated tertiary amines (known accelerators). This new compound exhibits mild latency, in addition to promoting backend cure of the given molded PU part. Examples of such ligands which fit the alkanolamine profile are N,N,N',N'-tetrakis(2-hydroxypropyl)ethylene diamine and N,N,N',N',-tetrakis(2-hydroxyethyl)ethylene diamine.

DETAILED DESCRIPTION

Bismuth carboxylates have been used as catalysts for polyurethane formation. Bismuth carboxylates are attractive catalysts as these compounds have low toxicity and a rapid cure rate. Yet, with conventional bismuth carboxylate catalysts, the window of reactivity may be too short, or the backend cure may result in a tacky finish. Accordingly, it would be desirable to have an improved bismuth catalyst with a longer reactivity period resulting in a smoother finished product with no tack.

The catalysts of the instant application are prepared by the reaction of a bismuth carboxylate salt with an alkanolamine. The carboxylate salt may have 2 to 20 carbon atoms in the molecule, preferably 8 to 12 carbon atoms in the molecule. The useful carboxylic acids are represented by the formula RCOOH wherein R is a hydrocarbon radical containing 1 to about 19 carbon atoms. R can be alkyl, cycloalkyl aryl, alkaryl such as methyl, ethyl, propyl, isopropyl, neopentyl, octyl, neononyl, cyclohexyl, phenyl, tolyl or napthyl. More specifically, the bismuth carboxylate is bismuth neodecanoate which is reacted with an alkanolamine to form the desired catalyst.

The catalysts of the present technology can be employed in a wide range of elastomer formulation systems where reduced catalyst toxicity is desirable. The catalyst provides an alternative to the use of catalysts based on lead, tin or mercury. The catalyst of this technology provides optimum performance based on tailored gel times, provides rapid release or remold times, and will not contribute to embrittlement of the cured elastomer. The catalyst of the instant technology, as a polymerization catalyst, has minimal effect on the water/isocyanate reaction with moisture levels normally found in a wet/undried formulated urethane system. Most importantly, the catalyst has an excellent acute toxicity profile. No occupational exposure limit standard must be met when using the catalyst.

In contrast to many conventional catalysts, bismuth may be considered a "green" metal which is safe for human consumption. It can found in applications such as bismuth subsalicylate (for nausea, heartburn, etc.), bismuth subgallate (internal deodorant), bismuth subnitrate/subsulfate (radiochemicals), bismuth oxychloride (in make-up), and bismuth brocathol (for eye infections).

The use of coordination or complexation ligands such as alkanolamines, when added to a conventional bismuth carboxylate has been found to mediate and control the initial and/or backend cure properties of bismuth-catalysts. Alkanloamines may include, but are not limited to N-methyldiethanolamine, N-methylethanolamine, Diethanolamine
Diisopropanolamine, N,N-diethylethanolamine, N,N-dimethylethanolamine, 2-(2-aminoethoxy)ethanol, 2-amino-2-methyl-1-propanol, 1-dimethylamino-2-propanol 2-(((2-dimethylamino)ethyl)methylamine)ethanol, 2-(butylamino)ethanol, 2-(ethylamino)ethanol, 2-(methylamino)ethanol, 1-amino-2-propanol, 3-amino-1-propanol.

Figure 1:
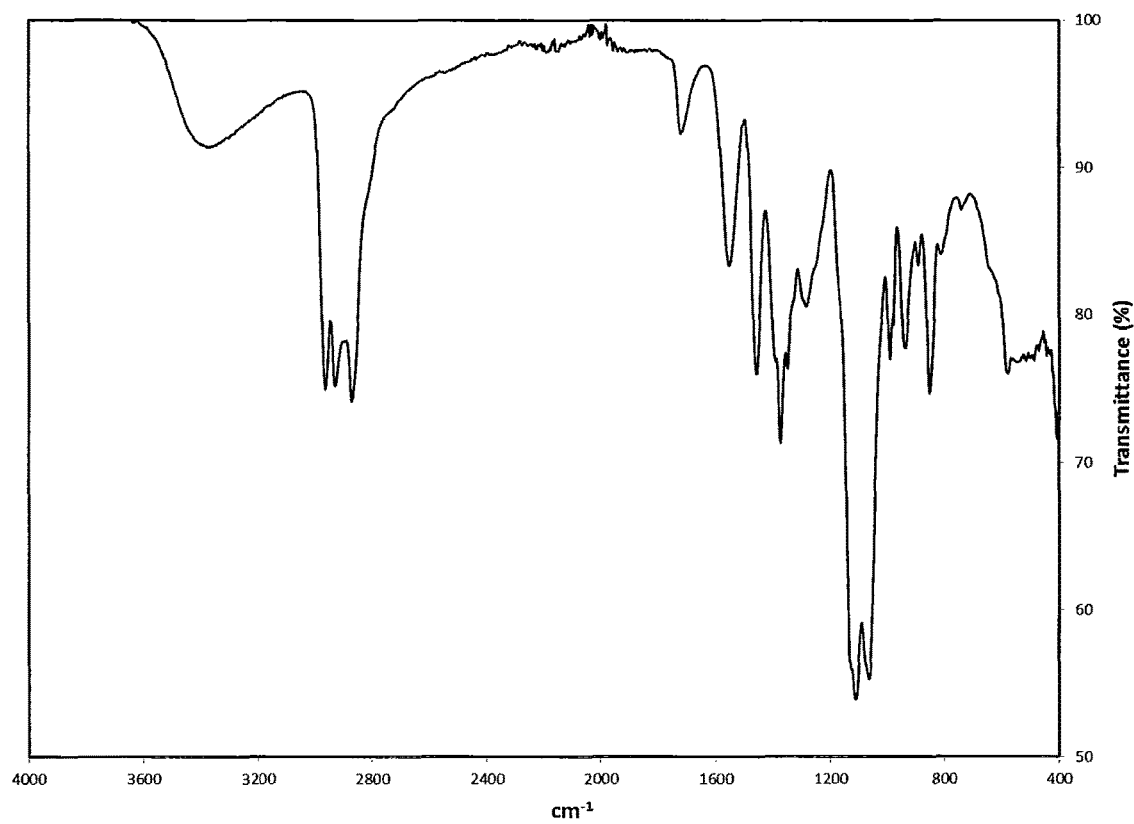
FIG. 1 is the FTIR spectrum for Curative 8840 in Example 1.
Figure 2:
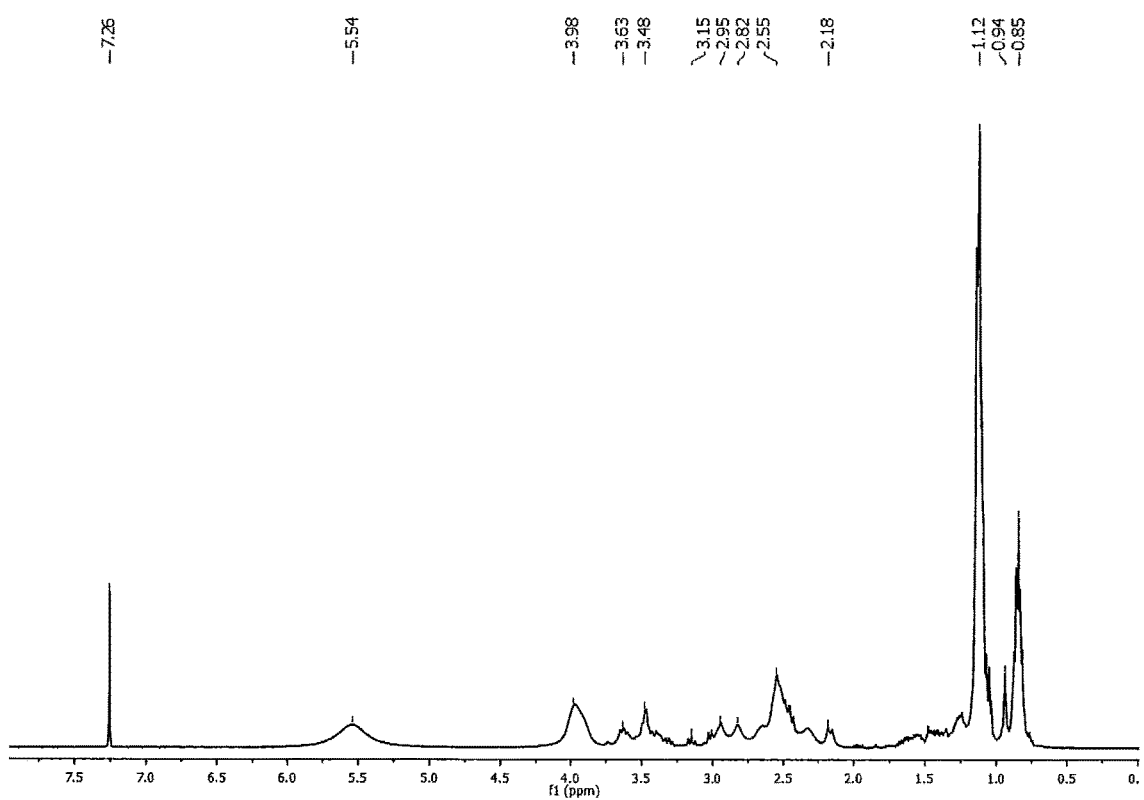
FIG. 2 is the $^1$H NMR spectrum for Curative 8840 in Example 1.
Figure 3:
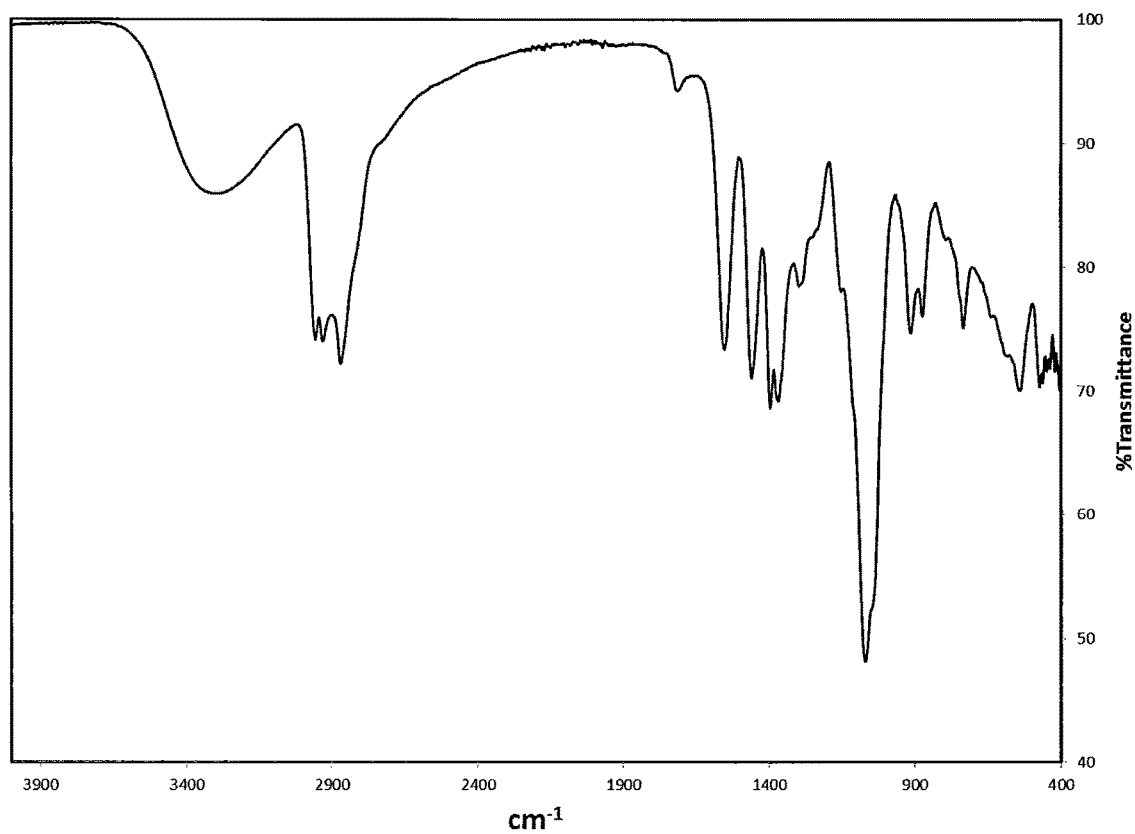
FIG. 3 is the FTIR spectrum for Curative 8842 in Example 2.
Figure 4:
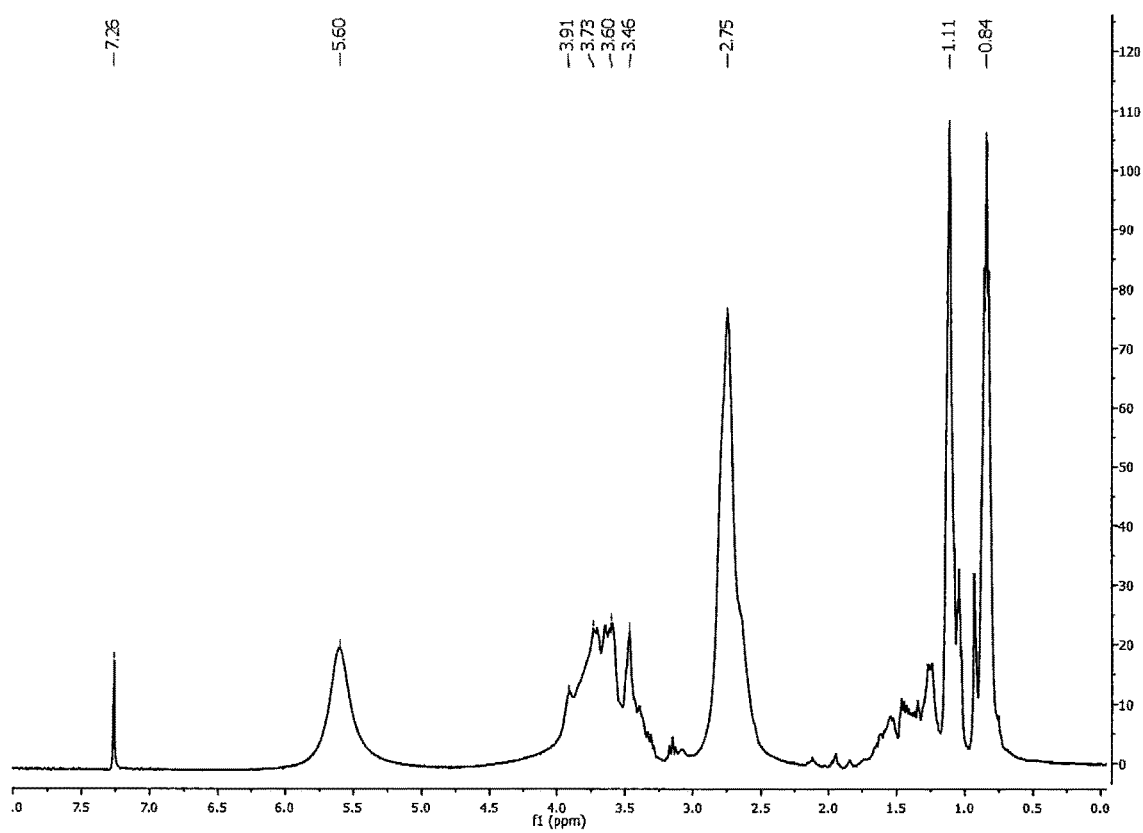
FIG. 4 is the $^1$H NMR spectrum for Curative 8842 in Example 2.

Additional examples of alkanolamine ligands are shown in FIG. 1:

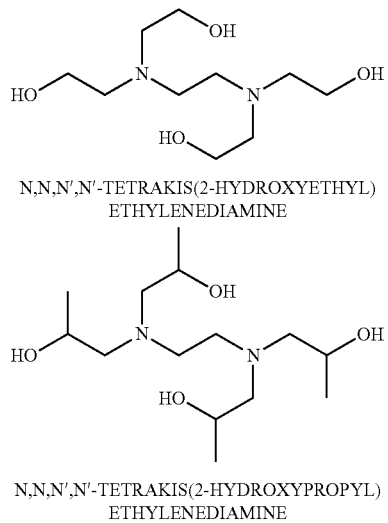

N,N,N',N'-TETRAKIS(2-HYDROXYETHYL) ETHYLENEDIAMINE

N,N,N',N'-TETRAKIS(2-HYDROXYPROPYL) ETHYLENEDIAMINE

The bismuth diaminotetraol complexes BiCAT 8840 and BiCAT 8842, (where BiCAT 8840 is bismuth, 1,1',1'',1'''-(1,2-ethanediyldinitrilo)tetrakis[2-propanol] neodecanoate complexes; and BiCAT 8842 is bismuth, 2,2',2'',2'''-(1,2-ethanediyldinitrilo)tetrakis[ethanol] neodecanoate complexes) may be used as catalysts in polymerization reactions, including use as polyurethane catalysts. A benefit of the use of these compounds is thought to be the combination of the bismuth carboxylate with the diaminotetraol ligands for use in the formation of polyurethane foam and CASE applications.

The ratio of alkanolamine to metal may be varied from 2.0: to 0.1 mole ratio to produce the desired cure profile, which is also based on selection of isocyanate (MDI and polyol (polyester, polyether, etc.)) to form the polyurethane. Temperature can also be varied in the polymerization process (temperature ranges of ambient temperature to 90° C.) to obtain the desired cure rate.

All catalysts used prior to this technology had the capability of promoting reaction between a hydroxyl group and isocyanates to produce urethane linkages and, ultimately, polyurethane products. The major disadvantage of these catalysts is that they contain metals including mercury and as such, must be handled with extreme caution due to their classification as poisons and the shipping containers must be labeled accordingly. Organolead catalysts must also be handled with a great deal of caution due to their toxicity classification as a hazardous substance. Primarily due to these questions regarding toxicity and handling, the use of tin catalysts in non-cellular urethane systems has become popular. As a class, tin compounds do not provide the same type of catalytic performance as mercury and lead compounds, since the tin compounds also promote the reaction between moisture and isocyanates in addition to the hydroxyl group-isocyanate reaction. The non-specific nature of the tin catalysts makes them difficult to use, with the processor required to go to extreme measures to reduce the presence of moisture in order to eliminate bubbling or pinhole formation in the elastomers obtained.

The hydroxy containing reactants used in the preparation of the polyurethane elastomers of the present technology comprise primary and secondary hydroxy terminated polyalkylene ethers and polyesters having from 2 to 4 hydroxyl groups and a molecular weight of from about 1000 to 10,000. They are liquids, or are capable of being dissolved or melted for handling.

Examples of polyalkylene polyols include linear and branched polyethers having a plurality of ether linkages and containing at least 2 hydroxyl groups and being substantially free from functional groups other than hydroxyl groups. Typical examples of the polyalkylene polyols which are useful in the practice of the technology are the polyethylene glycols, polypropylene glycols and polybutylene ether glycols. Linear and branched copolyethers of ethylene oxide and propylene oxide are also useful in preparing the elastomers of this technology. Those having molecular weights of from 2000 to 5000 are preferred. Polyethers having a branch chain network are also useful. Such branched chain polyethers are readily prepared from alkylene oxides and initiators having a functionality greater than 2.

Any organic di- or tri-isocyanate can be used in the practice of the present technology. Diisocyanates are preferred. Examples of suitable organic polyisocyanates are isophorone diisocyanate (weatherability), polyisocyanates, trimethylene diisocyanate, tetramethylene diisocyanate, pentamethylene diisocyanate and hexamethylene diisocyanate. Examples of aromatic diisocyanates include 2,4-tolylene diisocyanate, and 2,6-tolylene diisocyanate. In addition, methylene diphenyldiisocyanates and polymeric isocyanates based on methylene diphenyldiisocyanates can be employed.

The amount of polyisocyanate employed ranges from about 0.7 to 1.3 mole of NCO in the polyisocyanate per mole of active hydrogen in the polyols.

In certain instances it may be desirable to add a chain extender to complete the formulation of polyurethane polymers by reacting isocyanate groups of adducts or prepolymers. Examples of some types of polyol chain extenders include 1, 4-butanediol, diethylene glycol, trimethylol propane and hydroquinone di(beta hydroxyethyl ether).

The chain extender when present is added as 1 to 20 weight percent, preferably 3 to 6 weight percent based on the weight of the reactants. The technology is illustrated by the following specific but non-limiting examples.

Another aspect of this technology is the combination of alkanolamine ligands per metal center through substitution of the initial ligand, and/or displacement, with complexation. It is believed that unique polyurethane curative properties can be obtained either as synergistic or additive in nature.

In another aspect of the technology, when a bismuth-based catalyst such as BiCAT 8840 or BiCAT 8842 is used in the same formulation as the stannous octanoate at the same use level, the VOC's are the same for both BiCAT systems, confirming the catalysts of the present disclosure may be used as a suitable substitute for tin-based catalysts. This PU formulation is for interior automotive applications. Accordingly, in an industrial evaluation designed to analyze both VOC's and the interior fogging, the foam produced using the bismuth catalysts of the present technology have a cellular structure, comparable to the stannous octanoate catalyst. Importantly, measurement of VOC (fogging) under standardized automotive conditions showed that a PU formulation cured with TEDA had a VOC content of 208 ug/g, relative to the use of BiCAT 8840 which yielded a VOC content of 94 ug/g.

EXAMPLES

Example 1

Preparation of Curative 8840

To a 500 mL reaction flask with a nitrogen blanket, overhead stirrer, and temperature probe, is added 100 grams of BiCAT 8106, (bismuth neodecanoic acid, 20 wt % Bi). Begin agitation and warm to 35° C. After temperature is reached, charge 60 grams N,N,N',N'-tetrakis(2-hydroxypropyl)ethylenediamine. After adding, a small exotherm is observed along with a color change from yellow to orange. After exotherm subsides, 40 g of diethylene glycol monoethyl ether is charged. Agitate at medium speed for one hour. Raise the temperature to 45° C. and hold for one hour. The material is then poured into a sample cup with lid. Characterization, or "fingerprinting," of the 8840 is conducted by FTIR, $^1$H NMR, and metal concentration determination. Analytical measurement of the bismuth concentration was 10.1 wt %, with a quantitative yield.

Example 2

Preparation of Curative 8842

To a 500 mL reaction flask with a nitrogen blanket, overhead stirrer, temperature probe, is added 50 grams of BiCAT 8106, (bismuth NDA, 20 wt % Bi). Begin agitation and warm to 35° C. After temperature is reached, charge 50 grams N,N,N',N'-tetrakis(2-hydroxyethyl)ethylenediamine. After adding, a small exotherm is observed along with a color change from yellow to orange. Using medium agitation speed, continue to mix for one hour. Raise the temperature to 45° C. and hold for one hour. The material is then poured into a sample cup with lid. Characterization, or "fingerprinting," of the 8842 is conducted by FTIR, NMR, and metal concentration determination. Analytical measurement of the bismuth concentration was 10.7 wt %, with a quantitative yield.

Example 3

Spray Foam Formulation of Two-Component PU System Using Curative 8842

BiCAT 8842 was used in a two-part polyurethane system (TDI) for spray-foam applications. The BiCAT 8842 was added at 0.125 wt % to the polyol side (B-part). In addition, the polyol side contained 2.5 wt % water. It has been demonstrated that the 8842 remained stable for many weeks in the presence of moisture, while a control formulation using bismuth neodecanoate at the same use level began to turn white after ~14 min, sign of bismuth hydrolysis to the hydroxide. The same dosage of stannous octoate curative was added to the TDI-tin-based control formulation. The cure rate and gel time were similar to that of the stannous octoate.

Example 4

Foam Kinetics and Density of Two-Component PU System Using Curative 8842

A polyurethane formulation representative of typical foam compositions was tested with weight percent equivalent stannous octoate and BiCAT 8842 added with the other catalysts to the B side. The following composition was used:
A Side: Isocyanate TDI 80-20
B side: Polyester polyol OH number 60, F=2
Water (3.5 w/w)
Silicon surfactant (varied)
Catalyst: TEDA (Dabco) crystal (0.16% w/w)
BDMAEE (0.12% w/w)
BICAT 8842 (0.02% w/w) or stannous octoate (0.02% w/w)

The test showed the following reaction times and foam densities:

|  | 8842 | Stannous Octoate |
| --- | --- | --- |
| Cream time (min) | 14 | 15 |
| Tack free time (min) | 89 | 88 |
| Foam Density (kg/m$^3$) | 35.4 | 35.1 |

Example 5

Slabstock Foam Application of Two-Component PU System Using Curative 8842

During an industrial test, 13 meters of polyurethane slabstock foam matrix in continuous mode was produced and, from visual analysis, the foam matrix retains the same properties as did the stannous octoate formulation.

The following composition was used:
A Side:

| TDI 80-20 | 80% w/w |
| --- | --- |
| TDI 65 | 20% w/w |

B Side:

| Polyether polyol (OH = 28) | 90% w/w |
| --- | --- |
| Polymeric polyol: | 10% w/w |
| Water | 2.75% w/w |
| TEDA in DPG | 0.125% w/w |
| BDMAEE in DPG | 0.125% w/w |
| Siliconic copolymer | 2.05% w/w |
| Flame retardant | 6.0% w/w |
| Stannous octoate or BiCAT 8842 | 0.16% w/w |

Example 6

Accelerated Aging of Curatives

Accelerated aging of curatives 8840 and 8842 (2.0 pphp) in the presence of water (2.5 pphp) and temperature, as indicated in the Table below:

[Note: polyols supplied to Shepherd as their 4-component polyol systems by Huntsman.] BiCAT 8108 is bismuth neodecanoate, 20 wt % bismuth.

| Component | Use level |
|---|---|
| Terate 4020 | 60 parts |
| Voranol 470x | 30 parts |
| Jeffol SG 360 | 10 parts |
| TMCP | 20 parts |
| DI Water | 2.5 parts/4.0 parts |
| Curative | 2.0 parts |

| DI Water | Oven temperature | Curative | Stability | DAY |
|---|---|---|---|---|
| 2.5 parts | 130° F. | POLYOL MIX - CONTROL | transparent | 1 |
| " | " | BiCAT 8108 - CONTROL | transparent | 1 |
| " | " | 8842 | transparent | 1 |
| " | " | 8840 | transparent | 1 |
| 2.5 parts | 130° F. | POLYOL MIX - CONTROL | transparent | 2 |
| " | " | BiCAT 8108 - CONTROL | transparent | 2 |
| " | " | 8842 | transparent | 2 |
| " | " | 8840 | transparent | 2 |
| 2.5 parts | 130° F. | POLYOL MIX - CONTROL | transparent | 3 |
| " | " | BiCAT 8108 - CONTROL | transparent | 3 |
| " | " | 8842 | transparent | 3 |
| " | " | 8840 | transparent | 3 |
| 2.5 parts | 160° F. | POLYOL MIX - CONTROL | transparent | 4 |
| " | " | BiCAT 8108 - CONTROL | transparent | 4 |
| " | " | 8842 | transparent | 4 |
| " | " | 8840 | transparent | 4 |
| 4.0 parts | 160° F. | POLYOL MIX - CONTROL | transparent | 5 |
| " | " | BiCAT 8108 - CONTROL | very sl. hazy | 5 |
| " | " | 8842 | transparent | 5 |
| " | " | 8840 | transparent | 5 |
| " | " | POLYOL MIX - CONTROL | transparent | 6 |
| " | " | BiCAT 8108 - CONTROL | opaque; ppt formation | 6 |
| " | " | 8842 | transparent | 6 |
| " | " | 8840 | transparent | 6 |

What is claimed is:

1. A spray-foam polyurethane catalyst produced by the reaction between a bismuth carboxylate with an alkanolamine and a polyol, wherein polyol is selected from polyethylene glycols, polypropylene glycols and polybutylene ether glycols, wherein the bismuth carboxylate is bismuth neodecanoate, and wherein the alkanolamine is tetrakis(2-hydroxyethyl)ethylenediamine.

2. A polyurethane catalyst produced by the reaction between a bismuth carboxylate with an alkanolamine and a polyol, wherein polyol is selected from polyethylene glycols, polypropylene glycols and polybutylene ether glycols, wherein the bismuth carboxylate is bismuth neodecanoate, and wherein the alkanolamine is ethylenedinitrilo-tetra-2-propanol.

* * * * *